United States Patent
Hillman (10) Patent No.: US 11,364,194 B2
(45) Date of Patent: *Jun. 21, 2022

(54) COMPOSITIONS AND METHODS FOR THE MAINTENANCE OF ORAL HEALTH

(71) Applicant: ProBiora Health, LLC, Dallas, TX (US)

(72) Inventor: Jeffrey D. Hillman, Gainsville, FL (US)

(73) Assignee: ProBiora Health, LLC, Dallas, TX (US)

(*) Notice: Subject to any disclaimer, the term of this patent is extended or adjusted under 35 U.S.C. 154(b) by 150 days.

This patent is subject to a terminal disclaimer.

(21) Appl. No.: 16/909,624

(22) Filed: Jun. 23, 2020

(65) Prior Publication Data

US 2020/0315952 A1 Oct. 8, 2020

Related U.S. Application Data

(60) Continuation of application No. 15/946,665, filed on Apr. 5, 2018, now Pat. No. 10,688,038, which is a continuation of application No. 14/518,226, filed on Oct. 20, 2014, now Pat. No. 9,962,330, which is a continuation of application No. 13/017,214, filed on Jan. 31, 2011, now Pat. No. 8,865,156, which is a division of application No. 10/567,592, filed as application No. PCT/US2004/025899 on Aug. 10, 2004, now Pat. No. 7,931,892.

(60) Provisional application No. 60/494,169, filed on Aug. 11, 2003.

(51) Int. Cl.
| | |
|---|---|
| *A61K 8/99* | (2017.01) |
| *A61K 9/00* | (2006.01) |
| *A61K 9/68* | (2006.01) |
| *A61K 35/744* | (2015.01) |
| *A61Q 11/00* | (2006.01) |
| *A23L 33/135* | (2016.01) |
| *C12N 1/20* | (2006.01) |
| *A61K 35/00* | (2006.01) |

(52) U.S. Cl.
CPC .............. *A61K 8/99* (2013.01); *A23L 33/135* (2016.08); *A61K 9/0053* (2013.01); *A61K 9/0056* (2013.01); *A61K 9/0058* (2013.01); *A61K 35/744* (2013.01); *A61Q 11/00* (2013.01); *C12N 1/20* (2013.01); *A23Y 2240/81* (2013.01); *A61K 2035/115* (2013.01); *Y10S 435/822* (2013.01); *Y10S 435/885* (2013.01)

(58) Field of Classification Search
CPC ....................................................... A61K 8/99
See application file for complete search history.

(56) References Cited

U.S. PATENT DOCUMENTS

| | | | |
|---|---|---|---|
| 4,454,109 A | 6/1984 | Hillman | |
| 5,607,672 A | 3/1997 | Hillman | |
| 5,932,469 A | 8/1999 | Hillman | |
| 7,931,892 B2 | 4/2011 | Hillman | |
| 8,865,156 B2 | 10/2014 | Hillman | |
| 9,962,330 B2 | 5/2018 | Hillman | |
| 10,688,038 B2 * | 6/2020 | Hillman | ............... A61K 35/744 |

FOREIGN PATENT DOCUMENTS

| | | |
|---|---|---|
| EP | 0058575 A1 | 8/1982 |
| WO | 9640865 A1 | 12/1996 |
| WO | 9640975 A1 | 12/1996 |

OTHER PUBLICATIONS

Forssten et al., Nutrients "*Steptococcus* mutants, Caries and Simulation Models", Mar. 2, 2010(3), pp. 290-298, 2010.

Stashenko et al., "Microflora of Plaque in Rats following Infection with an LDH-Deficient Mutant of *Streptococcus rattus*", Carries Res., 23:375-377 (1989), Year: 1989.

Tagg et al., "Bacterial replacement therapy: adapting 'germ warfare' to infection prevention", Trends in Biotechnology, vol. 21 No. 5, May 2003, 7 pages.

* cited by examiner

*Primary Examiner* — Albert M Navarro

(74) *Attorney, Agent, or Firm* — Fish IP Law, LLP (57) ABSTRACT

The invention provides a probiotic formulation that includes an LDH-deficient *mutans streptococcus* strain and an attenuated *S. oralis* strain. *S. uberis* strains can be included in the probiotic formulation. Such a probiotic formulation is suitable for transiently colonizing the oral cavity with beneficial bacteria.

20 Claims, 4 Drawing Sheets

Specification includes a Sequence Listing.

Comparison of *S. mutans* JH145 LDH gene to *S. mutans* BHT-2 LDH gene.

*ldh* Start: base 486 (Bold)
JH145 mutation: 1 bp deletion at base 718 of BHT-2
*ldh* Stop: base 1474/BHT-2 and 1473/JH145 (<u>Underline</u>)

```
JH145:  191   tcacgaacatctggcagggcacgagaaacaataacactcatagcatagtcaataaaactc  250
              ||||||||||||||||||||||||||||||||||||||||||||||||||||||||||||
BHT-2:  191   tcacgaacatctggcagggcacgagaaacaataacactcatagcatagtcaataaaactc  250

JH145:  251   gttttcatttcactcgttaaattaacatctactaaatttctatcttgcattaaaaaatgc  310
              ||||||||||||||||||||||||||||||||||||||||||||||||||||||||||||
BHT-2:  251   gttttcatttcactcgttaaattaacatctactaaatttctatcttgcattaaaaaatgc  310

JH145:  311   tccatttctagtctaaaactcctttatattatatcacaaaaaatgctcttttcagctat   370
              ||||||||||||||||||||||||||||||||||||||||||||||||||||||||||||
BHT-2:  311   tccatttctagtctaaaactcctttatattatatcacaaaaaatgctcttttcagctat   370

JH145:  371   tctactatagttttcctttaacagaggaaaatactagtgacttttttaacaaaaagtgtt  430
              ||||||||||||||||||||||||||||||||||||||||||||||||||||||||||||
BHT-2:  371   tctactatagttttcctttaacagaggaaaatactagtgacttttttaacaaaaagtgtt  430

JH145:  431   agaataaattcgtataaaatatacacttaataaattataaggagatgtttagaacatgac  490
              ||||||||||||||||||||||||||||||||||||||||||||||||||||||||||||
BHT-2:  431   agaataaattcgtataaaatatacacttaataaattataaggagatgtttagaacatgac  490

JH145:  491   tgcaactaaacaacataaaaaagtcatccttgtcggtgatggtgctgtaggatcatctta  550
              ||||||||||||||||||||||||||||||||||||||||||||||||||||||||||||
BHT-2:  491   tgcaactaaacaacataaaaaagtcatccttgtcggtgatggtgctgtaggatcatctta  550

JH145:  551   cgccttcgcccttgttaaccaaggaatcgctcaagaactcggaattattgaaattcctca  610
              ||||||||||||||||||||||||||||||||||||||||||||||||||||||||||||
BHT-2:  551   cgccttcgcccttgttaaccaaggaatcgctcaagaactcggaattattgaaattcctca  610

JH145:  611   gctgtttgaaaaggctgttggagacgctcttgaccttagccatgcacttgccttcacttc  670
              ||||||||||||||||||||||||||||||||||||||||||||||||||||||||||||
BHT-2:  611   gctgtttgaaaaggctgttggagacgctcttgaccttagccatgcacttgccttcacttc  670

JH145:  671   accaaagaaaatttacgctgctaaatatgaagactgtgcggatgctg-ccttgttgtcat  729
              ||||||||||||||||||||||||||||||||||||||||||||||| ||||||||||||
BHT-2:  671   accaaagaaaatttacgctgctaaatatgaagactgtgcggatgctgaccttgttgtcat  730

JH145:  730   tactgcaggtgcacctcaaaaaccaggtgaaactcgtcttgaccttgtcggtaaaaacct  789
              ||||||||||||||||||||||||||||||||||||||||||||||||||||||||||||
BHT-2:  731   tactgcaggtgcacctcaaaaaccaggtgaaactcgtcttgaccttgtcggtaaaaacct  790
```

FIGURE 2B

```
JH145:  790  tgcaatcaacaaatctatcgttacacaagtggttgaatcaggctttaagggaatcttctt  849
             ||||||||||||||||||||||||||||||||||||||||||||||||||||||||||||
BHT-2:  791  tgcaatcaacaaatctatcgttacacaagtggttgaatcaggctttaagggaatcttctt  850

JH145:  850  ggttgctgccaacccagttgacatcttgacttattcaacatggaaattctcaggtttccc  909
             ||||||||||||||||||||||||||||||||||||||||||||||||||||||||||||
BHT-2:  851  ggttgctgccaacccagttgacatcttgacttattcaacatggaaattctcaggtttccc  910

JH145:  910  taaagaacgcgtcattggttctggtacatctcttgatactgctcgtttccgtcaagctct  969
             ||||||||||||||||||||||||||||||||||||||||||||||||||||||||||||
BHT-2:  911  taaagaacgcgtcattggttctggtacatctcttgatactgctcgtttccgtcaagctct  970

JH145:  970  tgctgaaaaaatcggggttgatgctcggtcagtccacgcctatatcatgggtgaacacgg  1029
             ||||||||||||||||||||||||||||||||||||||||||||||||||||||||||||
BHT-2:  971  tgctgaaaaaatcggggttgatgctcggtcagtccacgcctatatcatgggtgaacacgg  1030

JH145: 1030  tgattcagaatttgccgtttggtctcatgccaatgtagctggtgttaaattagaacaatg  1089
             ||||||||||||||||||||||||||||||||||||||||||||||||||||||||||||
BHT-2: 1031  tgattcagaatttgccgtttggtctcatgccaatgtagctggtgttaaattagaacaatg  1090

JH145: 1090  gctgcaagacaaccgtgatgttgatgctgaaggtctcgtaaaactgtttgtatctgttcg  1149
             ||||||||||||||||||||||||||||||||||||||||||||||||||||||||||||
BHT-2: 1091  gctgcaagacaaccgtgatgttgatgctgaaggtctcgtaaaactgtttgtatctgttcg  1150

JH145: 1150  tgatgctgcttattcaatcatcaacaaaaaggtgctactttctatggtatcgctgtcgc  1209
             ||||||||||||||||||||||||||||||||||||||||||||||||||||||||||||
BHT-2: 1151  tgatgctgcttattcaatcatcaacaaaaaggtgctactttctatggtatcgctgtcgc  1210

JH145: 1210  ccttgcccgtatcactaaagcaatcttggatgacgaaaacgccgttcttccgctttcagt  1269
             ||||||||||||||||||||||||||||||||||||||||||||||||||||||||||||
BHT-2: 1211  ccttgcccgtatcactaaagcaatcttggatgacgaaaacgccgttcttccgctttcagt  1270

JH145: 1270  tttccaatcaggccaatacgaaggtgttgaagatgtcttcatcggacagccggccatcgt  1329
             ||||||||||||||||||||||||||||||||||||||||||||||||||||||||||||
BHT-2: 1271  tttccaatcaggccaatacgaaggtgttgaagatgtcttcatcggacagccggccatcgt  1330

JH145: 1330  tggtgcacacggtatcgttcgtccagtaaatattccgttaaatgatgctgaactgcaaaa  1389
             ||||||||||||||||||||||||||||||||||||||||||||||||||||||||||||
BHT-2: 1331  tggtgcacacggtatcgttcgtccagtaaatattccgttaaatgatgctgaactgcaaaa  1390

JH145: 1390  aatgcaggcttctgctaaacagctgaaagcaatcattgacgaagctttctcaaatgaaga  1449
             ||||||||||||||||||||||||||||||||||||||||||||||||||||||||||||
BHT-2: 1391  aatgcaggcttctgctaaacagctgaaagcaatcattgacgaagctttctcaaatgaaga  1450

JH145: 1450  atttgctgctgctgcagctcgtaa 1473 SEQ ID NO:1
             ||||||||||||||||||||||||
BHT-2: 1451  atttgctgctgctgcagctcgtaa 1474 SEQ ID NO:9
```

FIGURE 2C

BHT-2 Protein Sequence where (—) indicates a stop codon (SEQ ID NO:10).

```
1   MTATKQHKKVILVGDGAVGSSYAFALVNQGIAQELGIIEIPQLFEKAVGD  50
51  ALDLSHALAFTSPKKIYAAKYEDCADADLVVITAGAPQKPGETRLDLVGK  100
101 NLAINKSIVTQVVESGFKGIFLVAANPVDILTYSTWKFSGFPKERVIGSG  150
151 TSLDTARFRQALAEKIGVDARSVHAYIMGEHGDSEFAVWSHANVAGVKLE  200
201 QWLQDNRDVDAEGLVKLFVSVRDAAYSIINKKGATFYGIAVALARITKAI  250
251 LDDENAVLPLSVFQSGQYEGVEDVFIGQPAIVGAHGIVRPVNIPLNDAEL  300
301 QKMQASAKQLKAIIDEAFSNEEFAAAAAR—                      329
```

JH145 Protein Sequence where (—) indicates a stop codon (SEQ ID NOs:2-8).

```
1   MTATKQHKKVILVGDGAVGSSYAFALVNQGIAQELGIIEIPQLFEKAVGD  50
51  ALDLSHALAFTSPKKIYAAKYEDCADAALLSLLQVHLKNQVKLVLTLSVK  100
101 TLQSTNLSLHKWLNQALRESSWLLPTQLTS—LIQHGNSQVSLKNASLVLV  150
151 HLLILLVSVKLLLKKSGLMLGQSTPISWVNTVIQNLPFGLMPM—LVLN—N  200
201 NGCKTTVMLMLKVS—NCLYLFVMLLIQSSTKKVLLSMVSLSPLPVSLKQS  250
251 WMTKTPFFRFQFSNQANTKVLKMSSSDSRPSLVHTVSFVQ—IFR—MMLNC  300
301 KKCRLLLNS—KQSLTKLSQMKNLLLLQLV                       329
```

COMPOSITIONS AND METHODS FOR THE MAINTENANCE OF ORAL HEALTH

PRIORITY

This application is a continuation application of U.S. patent application Ser. No. 15/946,665 filed Apr. 5, 2018, which is a continuation of U.S. patent application Ser. No. 14/518,226, filed Oct. 20, 2014, which is a continuation application of U.S. patent application Ser. No. 13/017,214, filed Jan. 31, 2011, now U.S. Pat. No. 8,865,156, which is a divisional application of U.S. patent application Ser. No. 10/567,592, filed Jun. 30, 2006, now U.S. Pat. No. 7,931,892, which is a U.S. National Phase filing of PCT/US04/025899, filed on Aug. 10, 2004, which claims the benefit of U.S. Provisional patent application Ser. No. 60/494,169, filed Aug. 11, 2003, all of which are incorporated herein in their entirety by reference.

BACKGROUND OF THE INVENTION

Dental caries is characterized by dissolution of the mineral portion of the tooth, which can result in pain and loss of viability of the tooth, necessitating costly repair or extraction of the tooth. Dental caries affects 50% of children aged 5-9 years, 67% of adolescents age 12-17 years, and 94% of adults aged ≥18 years in the US (Morbidity and Mortality Weekly Reports 51: 144-147, 2002). Clean teeth will not decay; however, even with vigorous cleaning it is difficult to keep teeth sufficiently clean. Various methods have been developed to prevent or alleviate dental caries including, for example, the addition of sodium fluoride, sodium silicofluoride or hydrofluosilicic acid to drinking water, and sodium fluoride or tin fluoride to topical preparations, including dentifrices and mouthrinses. The prevention of caries by coating teeth with polymeric materials or sealants has been used; however, these techniques are costly, can require etching of the teeth with phosphoric acid and can be effective only in young children who have not yet developed caries. Antibacterial agents, including antibiotics, have also been proposed as a treatment for dental caries. Antibiotics kill microorganisms that are responsible for producing acid in the mouth such as *Streptococcus mutans*, but antibiotics are not selective in the killing of oral bacteria and also kill beneficial bacteria present in the oral cavity. This can result in a microbial imbalance in the mouth, which can have serious consequences. Therefore, more effective methods for the treatment and prevention of dental caries are needed in the art.

*Actinobacillus actinomycetemcomitans* (Aa) is the principal etiologic agent of early-onset periodontitis including localized and generalized prepubertal periodontitis, localized and generalized juvenile periodontitis, and rapidly progressive or refractory adult periodontitis. Tooth loss is the ultimate detrimental effect of destructive periodontal disease. A national survey of the United States revealed a prevalence of localized juvenile periodontitis of 0.53% and of generalized juvenile periodontitis of 0.13%. Loe & Brown, *J. Periodontol.* 62:608-616 (1991). Findings from a number of studies corroborate the conclusion that early-onset disease is similar in other industrialized countries and is more frequent in developing countries. Loe & Brown, *J. Periodontol.* 62:608-616 (1991).

In addition, certain types of adult periodontitis, which in general are very common conditions affecting over half the adult population, are likely to be caused by a select group of microorganisms indigenous to the oral cavity. These include Aa, *Porphyromonas gingivalis, Prevotella intermedia, Bacteroides forsythus, Treponema denticola, Campylobacter rectus* and *Eikenella corrodens*. There are antibiotic, surgical, and mechanical therapies for the treatment of the various types of periodontitis, but no means for prevention. Tetracycline has been widely used in the treatment of early-onset periodontitis. There remains a concern, however, of strains developing resistance to tetracycline as well as the possibility of overgrowth of other pathogenic microorganisms. Given the incidence of periodontal diseases, safe preventative and treatment strategies are needed in the art. Control of periodontal disease is also very important in light of recent attention to the possible role of periodontal infections as risk factors for systemic disease (e.g., coronary heart disease). Therefore, methods of treatment and prevention of early-onset periodontitis, localized and generalized juvenile periodontitis, and rapidly progressive or refractory adult periodontitis are needed in the art.

BRIEF SUMMARY OF THE INVENTION

The instant invention provides methods and compositions for the maintenance of oral health, such as the treatment and/or prevention of periodontitis, dental caries, *Candida* or fungal overgrowth in an oral cavity, halitosis, xerostomia-induced dental caries, oral bacterial infections or diseases, and oral wounds. In one embodiment the invention provides probiotics for the maintenance of oral health.

Probiotics are viable single or mixed culture microorganisms, which when applied to animals or humans, beneficially affect their host by improving the properties of the indigenous microflora. Traditionally, probiotic use has focused on the general category of gastrointestinal health, but the approach of using beneficial organisms has been suggested to prevent or treat other conditions, including application to maintain vaginal and urinary tract health. In the instant invention probiotics are used to maintain oral health.

One embodiment of the invention provides a composition comprising one or more isolated *Streptococcus oralis* strains and/or one or more *S. uberis* strains combined with one or more isolated *mutans streptococcus* strains that are lactate dehydrogenase-deficient. The *mutans streptococcus* strains can be one or more LDH-deficient strains of *S. rattus, S. cricetus, S. mutans, S. sobrinus, S. downeii, S. macacae*, and *S. ferus*. The composition can further comprise a carrier. The *mutans streptococcus* strain can be a naturally-occurring strain or a genetically modified strain that is lactate dehydrogenase-deficient. A *mutans streptococcus* strain can be, for example, a *S. rattus* strain JH145. A *S. oralis* strain can be, for example, *S. oralis* strain KJ3 or KJ3sm. A *S. uberis* strain can be, for example, KJ2 or KJ2 sm.

Another embodiment of the invention provides a food composition comprising one or more isolated *S. oralis* strains and/or one or more isolated *S. uberis* strains, and one or more isolated *mutans streptococcus* strains, wherein the *mutans streptococcus* strains are lactate dehydrogenase-deficient.

Still another embodiment of the invention provides a dentifrice, chewing gum, lozenge, oral rinse, or topical agent composition comprising one or more isolated *S. oralis* strains and/or one or more isolated *S. uberis* strains, and one or more isolated *mutans streptococcus* strains, wherein the *mutans streptococcus* strains are lactate dehydrogenase-deficient.

Yet another embodiment of the invention provides a method for maintaining oral health of a subject comprising administering to an oral cavity of a subject a composition comprising one or more isolated *S. oralis* strains and/or one or more isolated *S. uberis* strains and one or more isolated *mutans streptococcus* strains, wherein the *mutans streptococcus* strains are lactate dehydrogenase-deficient. The composition can be administered to the subject about once a day, about once a week or about once a month. The subject can be a mammal, such as a human. Maintaining oral health can comprise the treatment, prevention, or both treatment and prevention of periodontitis, dental caries, *Candida* or fungal overgrowth, halitosis, xerostomia-induced dental caries or periodontitis, oral bacterial infections or diseases, oral wounds or a combination thereof.

Even another embodiment of the invention provides a method of non-persistently colonizing an oral cavity of a subject with therapeutically-effective bacteria comprising administering to the oral cavity of a subject a combination comprising one or more isolated *S. oralis* strains and/or one or more isolated *S. uberis* strains, and one or more isolated *mutans streptococcus* strains, wherein the *mutans streptococcus* strains are lactate dehydrogenase-deficient. The subject can be a mammal, such as a human.

Therefore, the invention provides methods and compositions for the maintenance of oral health, including, for example, the prevention and/or treatment of dental caries, periodontitis, *Candida* or fungal overgrowth, halitosis, or xerostomia-induced dental caries or periodontal disease oral bacterial infections or diseases, oral wounds or a combination thereof.

DETAILED DESCRIPTION OF THE INVENTION

Probiotics can be defined as the administration of live microorganisms in adequate amounts to confer a health benefit on the host. Though originally developed for "gut health", probiotics are now being investigated in immune system modulation, vaginal and urinary tract health, allergies, inflammatory disorders and hypertension. Bacteria are normal inhabitants of humans, and the oral cavity provides an ecological niche for over 300 microbial species. Microbial interactions are logically of enormous importance in controlling the ecology of dental plaque and, thus, the outcome: oral health or disease. One preventive approach is to encourage colonization and growth of protective species or the establishment of a microbial flora that is balanced in favor of health. Beneficial effects can involve the production of a specific enzyme(s) or metabolite(s), or the probiotic organism can also cause the body to produce the beneficial action. A beneficial effect can also be achieved by inhibition of colonization or outgrowth of a pathogenic microorganism by competition for nutrients or attachment sites.

The invention provides compositions, therapeutic systems and methods of use for the maintenance of oral health including, for example, the treatment and/or prevention of dental caries, periodontitis, oral bacterial infections and diseases, oral wounds, *Candida* or fungal overgrowth, halitosis, or xerostomia-induced dental caries or periodontal disease, the promotion of wound healing, or a combination thereof in a subject. A composition of the invention comprises a therapeutically effective amount of one or more isolated strains of LDH-deficient *mutans streptococcus* in combination with a therapeutically effective amount of one or more isolated strains of *S. oralis* and/or one or more isolated strains of *S. uberis*.

Streptococcus oralis and Streptococcus uberis

*Streptococcus oralis* (previously known as *S. sanguis* Type II) and *S. uberis* are important components in maintaining the normal, healthy balance of microorganisms that compose the periodontal flora. See, Socransky et al., Oral Microbiol. Immunol. 3:1-7 (1988); Hillman and Shivers, Arch. Oral. Biol., 33:395-401 (1988); Hillman, et al., Arch. Oral. Biol., 30:791-795 (1985). *S. oralis* produces hydrogen peroxide, which can inhibit periodontal pathogens such as *Actinobacillus actinomycetemcomitans* (Aa), *Bacteroides forsythus*, and *P. intermedia*. Therefore, *S. oralis* and *S. uberis* can be useful in the maintenance of oral health. Compositions of the invention comprise one or more isolated strains of *S. oralis*, for example, ATCC 35037, ATCC 55229, ATCC 700233, ATCC 700234 and ATCC 9811. Other strains of *S. oralis* include KJ3 and KJ3sm. KJ3sm is a naturally occurring genetic variant of KJ3 that is resistant to streptomycin. The streptomycin resistance is advantageous because it provides a marker for easy isolation of the bacteria. Additionally, streptomycin resistant strains are slightly attenuated and do not survive as long in an oral cavity as wild-type strains. This property is useful where the goal is to non-persistently colonize the oral cavity of an animal with the bacteria.

*S. uberis* in plaque has been found to correlate with periodontal health, in particular by interfering with the colonization by periodontal pathogens such as *Porphyromonas gingivalis, Campylocbacter recta,* and *Eikenella corrodens*. Compositions of the invention can comprise one or more isolated strains of *S. uberis*, for example, ATCC 13386, ATCC 13387, ATCC 19435, ATCC 27958, ATCC 35648, ATCC 700407, ATCC 9927, strain KJ2 or strain KJ2sm. KJ2sm is a naturally occurring genetic variant of KJ2. That is streptomycin resistant and provides the same advantages as for streptomycin-resistant strains of *S. oralis*. One or more isolated strains of *S. oralis* or one or more isolated strains of *S. uberis*, or both, can be used in compositions and methods of the invention.

Mutans Streptococcus

Compositions of the invention comprise one or more isolated *mutans streptococcus* bacteria species deficient in the production of lactic acid. These strains include, for example, *S. rattus, S. cricetus, S. mutans, S. sobrinus, S. downeii, S. macacae,* and *S. ferus*. A *mutans streptococcus* strain of the invention does not substantially produce L(+) lactate dehydrogenase (LDH). Such a strain is termed an LDH-deficient strain. An LDH-deficient strain of *mutans streptococcus* produces 75%, 80%, 90%, 95%, 98%, 99%, or 100% less lactic acid than wild-type strains of *mutans streptococcus*. An LDH-deficient *mutans streptococcus* strain can be a naturally occurring strain of *mutans streptococcus* or a genetically modified strain of *mutans streptococcus*. LDH-deficient *mutans streptococcus* can compete with and/or displace pathogenic bacteria such as *S. mutans*, a principal etiological agent of dental caries, in the oral cavity. LDH-deficient *mutans streptococcus* stains will compete with *S. mutans* for the same nutrients, colonization sites, etc. in an oral cavity when administered as a probiotic. Therefore, LDH-deficient *mutans streptococcus* strains can be used to, for example, prevent and/or treat dental caries. LDH-deficient strains of *mutans streptococcus* are non-pathogenic, alter the microenvironment of the oral cavity to prevent colonization or outgrowth of pathogenic organisms, and/or displace pathogenic organisms from the oral cavity where the pathogen is part of the host's indigenous flora.

Figure 2A:
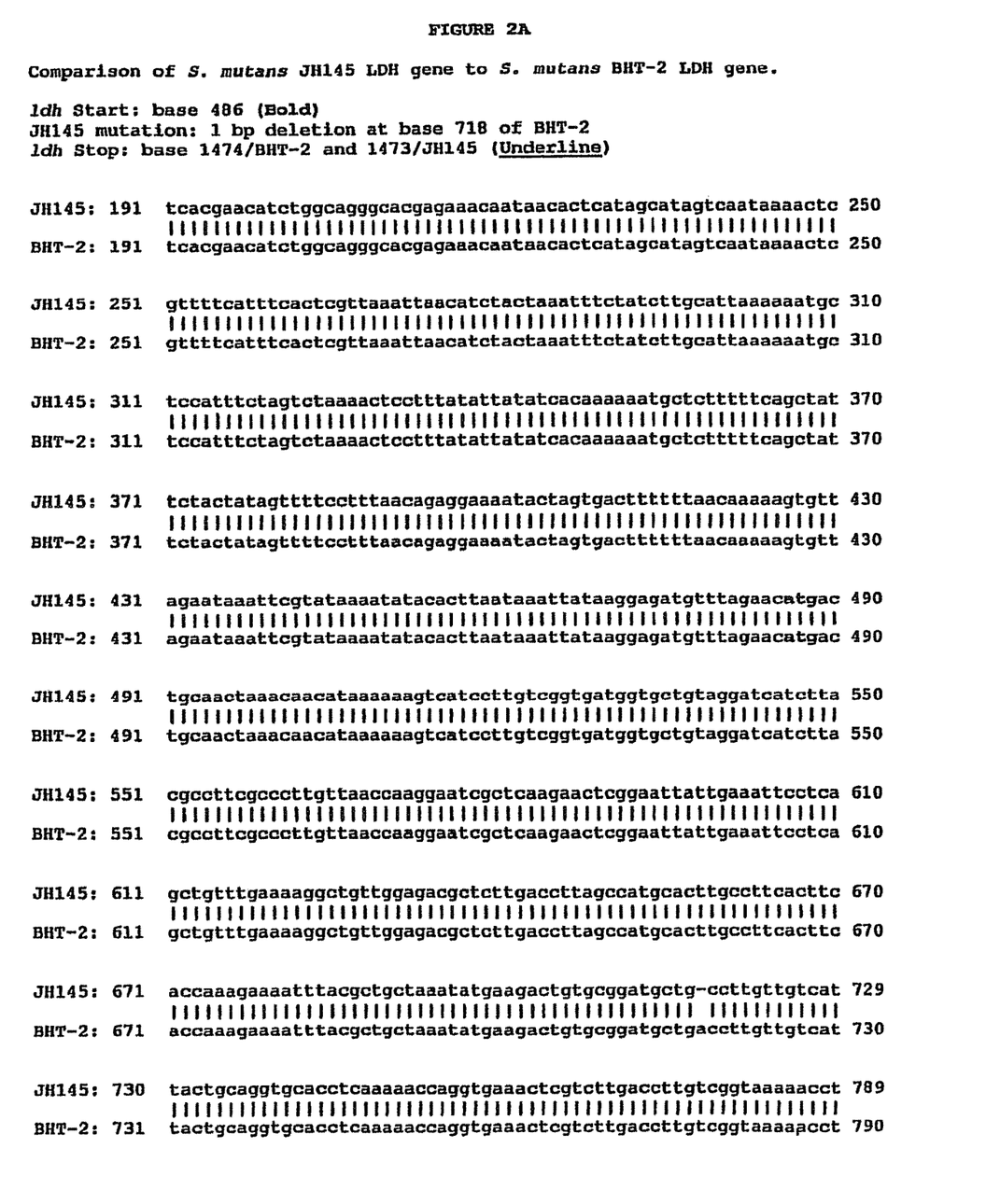
FIGS. 2A-C show the comparison of a *S. mutans* JH145 ldh gene to a *S. mutans* BHT-2 ldhgene and the corresponding protein sequences.
Figure 2B:
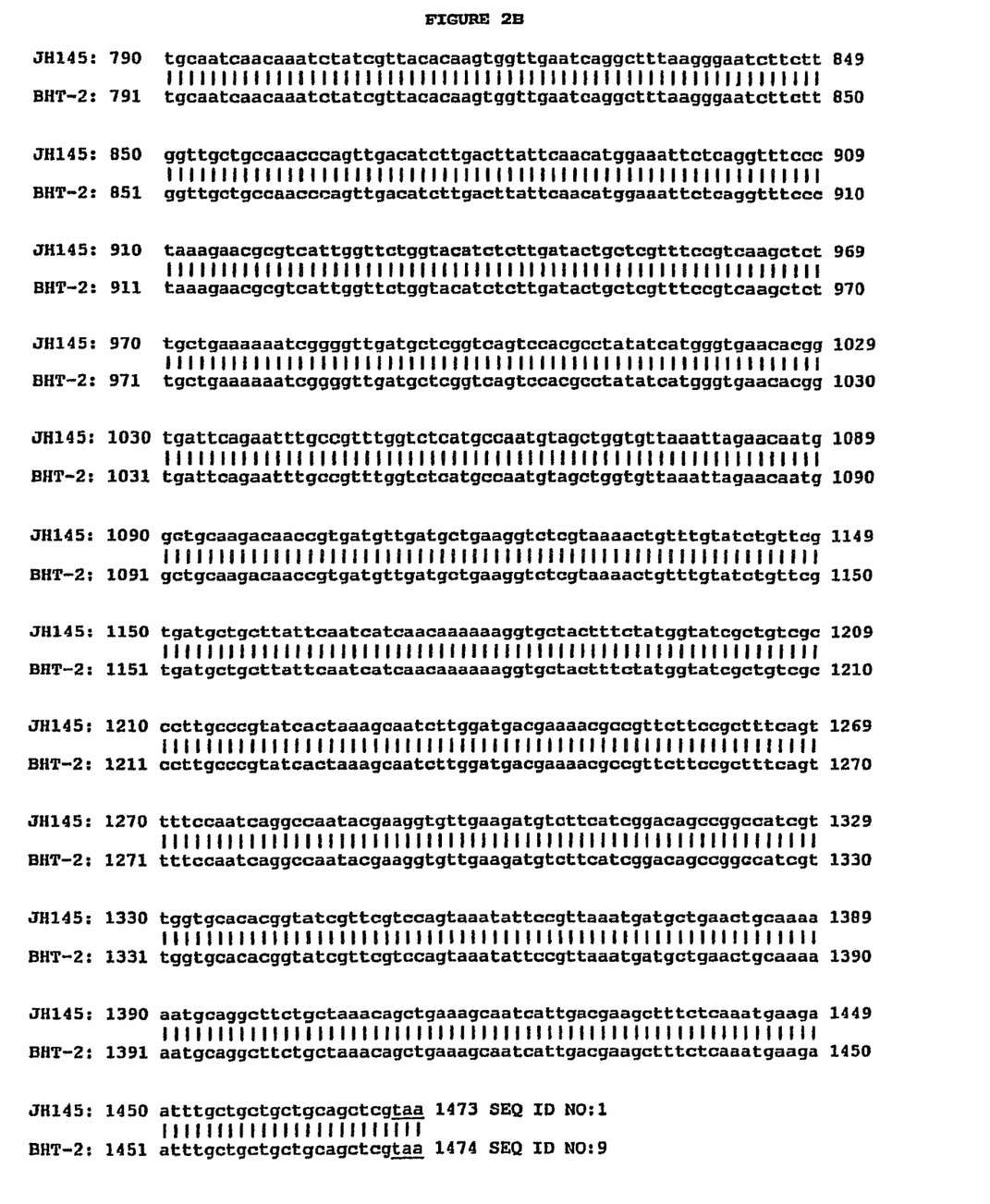
Figure 2C:
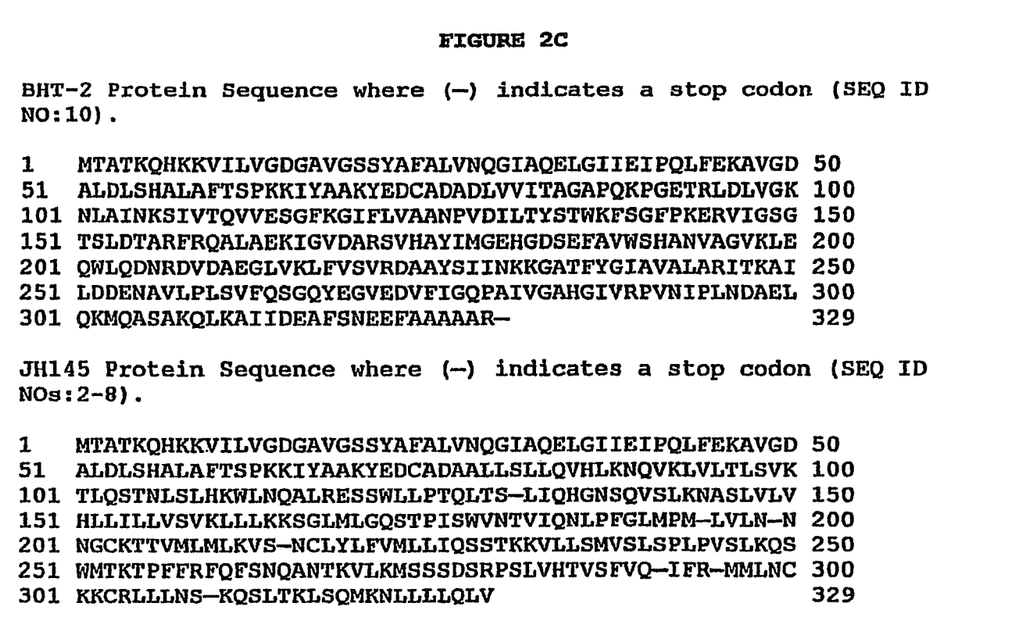

Examples of LDH-deficient *mutans streptococcus* strains include, for example, *S. rattus* JH145 (ATCC 31377) (a spontaneous, naturally-occurring LDH-deficient mutant) (See FIGS. 2A-C for a JH145 mutant LDH nucleotide and polypeptide sequence) and JH140 (ATCC 31341) (a chemically-modified LDH-deficient mutant). See e.g., Stanshenko & Hillman, Microflora of plaque in rats following infection with an LDH-deficient mutant of *Streptococcus rattus*, Caries Res. 23:375-377 (1989); Hillman, Lactate dehydrogenase mutants of *Streptococcus mutans*: Isolation and preliminary characterization. Infect. Immun. 21:206-212 (1978); see also Abhyankar et al., Serotype c *Streptococcus mutans* mutatable to lactate dehydrogenase deficiency. J Dent Res 1985 November; 64(11):1267-71.

An LDH-deficient strain of *mutans streptococcus* can be derived from a *mutans streptococcus* strain using, for example, chemical or physical mutagenesis techniques. Strains that are mutagenized using these techniques are considered genetically modified strains. For example, a *mutans streptococcus* strain can be subjected to mutagens such as nitrous acid, formic acid, sodium bisulphate, UV light, base analog mutagens, including for example, 5-bromo-deoxyuridine (5BU), alkylators such as ethyl methane sulfonate (EMS), methyl methane sulfonate (MMS), diethylsulfate (DES), and nitrosoguanidine (NTG, NG, MNNG). See e.g., In Vitro Mutagenesis Protocols, Braman, Ed., Humana Press, 2002.

Naturally-occurring, spontaneous LDH-deficient *mutans streptococcus* strains can be prepared using methods disclosed in, for example, Hillman, Lactate dehydrogenase mutants of *Streptococcus mutans*: isolation and preliminary characterization. Infect. Immun. 21:206-212 (1978). Spontaneous LDH-deficient mutants occur at the rate of approximately $10^{-5}$ frequency. See Johnson et al., Cariogenic potential in vitro in man and in vivo in the rat of lactate dehydrogenase mutants of *Streptococcus mutans*. Arch. Oral Biol. 25:707-713 (1980).

Naturally-occurring, spontaneous LDH-deficient strains of *mutans streptococcus* can be differentiated from LDH-producing strains of *mutans streptococcus* by plating the bacteria on glucose tetrazolium medium. LDH-deficient *mutans streptococcus* colonies will be bright red and relatively larger in size than colonies of the parent strain, which are white and relatively smaller in size on the glucose tetrazolium medium. Naturally-occurring, spontaneous LDH-deficient strains of *mutans streptococcus* can be used in a composition of the invention.

An LDH-deficient strain of *S. rattus* has been isolated. Briefly, a culture of *S. rattus* BHT-2 was grown overnight to saturation in Todd Hewitt broth, and diluted samples were spread on glucose tetrazolium medium to give approximately 300 colonies per plate. Wild-type, acid producing colonies are white on this medium. LDH-deficient mutants are bright red. *S. rattus* JH145 was one red colony amid approximately 100,000 white colonies that were screened. *S. rattus* JH145 is therefore a naturally-occurring, LDH-deficient mutant.

LDH-deficient strains of *mutans streptococcus*, such as LDH-deficient mutants of *S. rattus* BHT-2, produce less total titratable acid when incubated in the presence of glucose and other sugars or polyols, make substantially less lactic acid when incubated in the presence of glucose in the case of resting and growing cultures, adhere better to hydroxyapitite and accumulate more plaque when grown in the presence of sucrose. LDH activity can be assayed as described by Brown & Wittenberger (J. Bacteriol. 110:604, 1972).

Terminal pH can be determined by subculturing strains (1:100) in Todd-Hewitt broth containing 1% glucose. After 48 hours incubation in candle jars at 37° C., the absorbance at 580 nm and pH of the cultures can be determined. Lactic acid concentration of cultures can be determined by gas-liquid chromatography. See Salanitro & Muirhead, Quantitative method for the gas chromatographic analysis of short-chain monocarboxylic and dicarboxylic acids in fermentation media. Appl. Microbiol. 29:374-381 (1975); Hillman et al., Acetoin production by wild-type strains and a lactate dehydrogenase-deficient mutant of *Streptococcus mutans*. Infect. Immun. 55:1399-1402 (1987).

Additionally, any genetic modification techniques known to those of skill in the art can be used to create an LDH-deficient *mutans streptococcus* strain from an LDH-producing *mutans streptococcus* parent strain. For example, an LDH gene or a portion of an LDH gene can be deleted or mutagenized, including, for example, insertional mutagenesis techniques. Other mutagenesis techniques include, for example, homologous recombination, recursive sequence recombination, oligonucleotide-directed mutagenesis, site-directed mutagenesis, error-prone PCR, phosphothioate-modified DNA mutagenesis, uracil-containing template mutagenesis, gapped duplex mutagenesis, point mismatch repair mutagenesis, repair-deficient host strain mutagenesis, radiogenic mutagenesis, deletion mutagenesis, restriction-selection mutagenesis, restriction-purification mutagenesis, site saturation mutagenesis, ensemble mutagenesis, recursive ensemble mutagenesis, and chimeric nucleic acid creation. Therefore, any genetic modification technique that disables an LDH gene can be used to produce an LDH-deficient *mutans streptococcus* strain.

In one embodiment of the invention, the LDH-deficient strains, whether naturally-occurring or genetically-modified mutants, have a reversion frequency less than $10^{-7}$ and produce less than 10% of the parental level of lactate dehydrogenase activity.

Compositions of the Invention

Compositions of the invention comprise one or more isolated strains of *mutans streptococcus* combined with one or more isolated strains of *S. oralis*, or one or more isolated strains of *S. uberis*, or both one or more isolated strains of *S. oralis* and one or more isolated strains of *S. uberis*, wherein the *mutans streptococcus* strain is lactate dehydrogenase (LDH)-deficient. The combination of LDH-deficient *mutans streptococcus* with *S. oralis* and/or *S. uberis* provides a significant practical advantage in that the combination can used to prevent and treat, for example, both dental caries and periodontitis. Treatment of dental caries and/or periodontitis means that one or more symptoms of dental caries and/or periodontitis is alleviated, reduced, prevented or ameliorated either permanently or temporarily. Compositions and methods of the invention can also be used to treat or prevent *Candida* or fungal overgrowth in an oral cavity, due to, for example, antibiotic treatment, to treat or prevent halitosis (bad breath), and to treat or prevent dental caries and/or periodontitis associated with xerostomia (dry mouth), to treat or prevent oral bacterial infections or diseases, to treat or prevent oral wounds and combinations thereof.

*Mutans streptococcus*, *S. oralis* and/or *S. uberis* strains of the invention can be present in any therapeutically effective ratio. Therapeutically effective means effective to alleviate, reduce, prevent and/or ameliorate one or more symptoms of dental caries, periodontitis, bacterial infections or diseases, oral wounds, *Candida* or fungal overgrowth, halitosis, or xerostomia-induced dental caries or periodontal disease or a combination thereof either permanently or temporarily. Therapeutically effective also means effective to promote wound healing in an oral cavity.

The bacterial strains of the invention can further comprise a pharmaceutically acceptable or nutritionally acceptable carrier. The carrier is physiologically compatible with the oral cavity of the subject to which it is administered. Carriers can be comprised of solid-based, dry materials for formulation into tablet, capsule, lozenge, or powdered form. A carrier can also be comprised of liquid or gel-based materials for formulations into liquid, gel, and chewing gum forms.

Suitable liquid or gel-based carriers include but are not limited to: water, physiological salt solutions, urea, alcohols and derivatives, and glycols (e.g., ethylene glycol or propylene glycol). Compositions of the invention can also include natural or synthetic flavorings and food-quality coloring agents, all of which are compatible with maintaining viability of the bacterial strains of the invention. Thickening agents can also be added to compositions of the invention such as corn starch, guar gum, carbopol, and xanthan gum.

Flavorings and/or colorants can also be included in the carrier. Compositions of the invention can also include a plasticizer such as glycerol or polyethylene glycol. The composition of the carrier can be varied so long as it does not interfere significantly with the therapeutic activity of the bacterial strains of the invention.

A composition can be formulated to be suitable for oral administration in a variety of ways, for example in a liquid, a dried mass, a dentifrice, a mouth wash, an oral rinse, a liquid suspension, a topical agent, a powdered food supplement, a paste, a gel, a solid food, a packaged food, a wafer, lozenge, chewing gum and the like. Other formulations will be readily apparent to one skilled in the art. A composition of the invention can include a nutrient supplement component and can include any of a variety of nutritional agents, as are well known, including vitamins, minerals, essential and non-essential amino acids, carbohydrates, lipids, foodstuffs, dietary supplements, and the like.

Bacteria of the invention can be prepared in, for example, a fermenter. The bacteria can be harvested from the fermenter and can be, for example, concentrated. Bacteria of the invention can be prepared for use by, for example, dehydration or spray drying. Spray drying generally comprises spraying a suspension of bacteria in a vessel and under a steam of hot air. Bacteria can also be prepared for use by microencapsulation (see e.g., U.S. Pat. No. 6,251,478), freeze-drying, or by coating with a protective substance such as, for example, lipid material such as triacylglycerols, waxes, organic esters, soybean oil, cottonseed oil, palm kernel oil, and esters of long-chain fatty acids and alcohols.

Methods of Maintaining Oral Health

Pathogenic bacteria, such as *S. mutans* and *Actinobacillus actinomycetemcomitans*, which can colonize an oral cavity of an animal, can be inhibited and/or controlled by administering a composition comprising one or more LDH-deficient *mutans streptococcus* strains and one or more isolated *S. oralis* strains, or one or more isolated *S. uberis* strains, or both one or more isolated *S. oralis* strains and one or more isolated *S. uberis* strains to an oral cavity. Compositions can be administered to an oral cavity of a subject such as an animal, including a mammal, for example, a human, a non-human primate, a dog, a cat, a rat, a mouse, a horse, a goat, or a rabbit. The bacterial strains of the invention can form at least a part of the transient or indigenous flora of an oral cavity and exhibit beneficial prophylactic and/or therapeutic effects in the cavity.

The invention provides methods for the treatment, prevention, or both treatment and prevention of dental carries, periodontitis, *Candida* or fungal overgrowth, halitosis, or xerostomia-induced dental caries or periodontal disease oral bacterial infections or diseases, oral wounds or a combination thereof comprising administering a composition of the invention to an oral cavity of a subject. Periodontitis includes, for example, early-onset periodontitis, localized and generalized juvenile periodontitis, and rapidly progressive or refractory adult periodontitis. The composition is administered to the subject about once a day, about once a week or about once a month.

The compositions of the invention can be orally administered in for example, food, water, a dentifrice, a gel, a paste, an emulsion, aerosol spray, chewing gum, lozenge, tablet, capsule, or a liquid suspension. The bacteria can either be already formulated into food, water, gel or other carrier or can be a composition that is added to the carrier by the user prior to consumption.

One embodiment of the invention provides a method of non-persistently colonizing an oral cavity of a subject with therapeutically-effective bacteria comprising administering to the oral cavity of a subject a combination comprising one or more isolated strains of *S. oralis* and/or *S. uberis* and one or more isolated strains of *mutans streptococcus* organisms, wherein the *mutans streptococcus* organisms are lactate dehydrogenase-deficient. In one embodiment of the invention the administered bacterial strains do not permanently colonize the oral cavity, rather the strains are present in the oral cavity for about 1 day, about 1 week, about 2 weeks, about 3 weeks, about 1 month, about 2 months or about 3 months after administration of the bacteria. Optionally, the bacteria can permanently and persistently colonize the oral cavity of a subject.

Compositions of the invention can be administered at a dose of about $1 \times 10^3$, $1 \times 10^5$, $1 \times 10^7$, $1 \times 10^9$, or $1 \times 10^{11}$ CFU of viable bacteria. One, two, or more doses can be administered per day for about 1 week, about 2 weeks, about 1 month, about 2 months, about 3 months, about a year or more. Alternatively, a dose can be administered about every other day, about once a week, about once a month or about yearly.

Example 1

*Mutans* streptococci for Maintenance of Oral Health

Daily treatment with JH145 results in decreased levels of indigenous *Streptococcus mutans* because of competition for nutrients, attachment sites, and other factors. The reduced levels of indigenous *S. mutans* promotes dental health, since this microorganism is closely associated with dental caries.

Seventy-two weanling (24 day-old) Sprague-Dawley rats were infected with *S. mutans* strain NG8 by pipetting 100 microliters of a suspension containing approximately $10^{10}$ cells per ml into their mouths using a micropipettor. The infection regimen was repeated twice on consecutive days. The animals were maintained on diet TD 80406 (Harlan Teklad) and water ad lib, caged separately. NG8 was allowed to establish itself for 4 weeks. The animals were randomly divided into 6 groups of 12 and treated daily for 16 weeks as follows:

a. Animals in group 1 received 100 microliters of a suspension of JH145 containing $10^{10}$ cells per ml using a micropipettor.

b. Animals in group 2 received 100 microliters of a suspension of JH145 containing $10^9$ cells per ml using a micropipettor.
c. Animals in group 3 received 100 microliters of a suspension of JH145 containing $10^8$ cells per ml using a micropipettor.
d. Animals in group 4 received 100 microliters of a suspension of JH145 containing $10^7$ cells per ml using a micropipettor.
e. Animals in group 5 received 100 microliters of a suspension of JH145 containing $10^6$ cells per ml using a micropipettor.
f. Animals in group 6 are sham treated.

Figure 1:
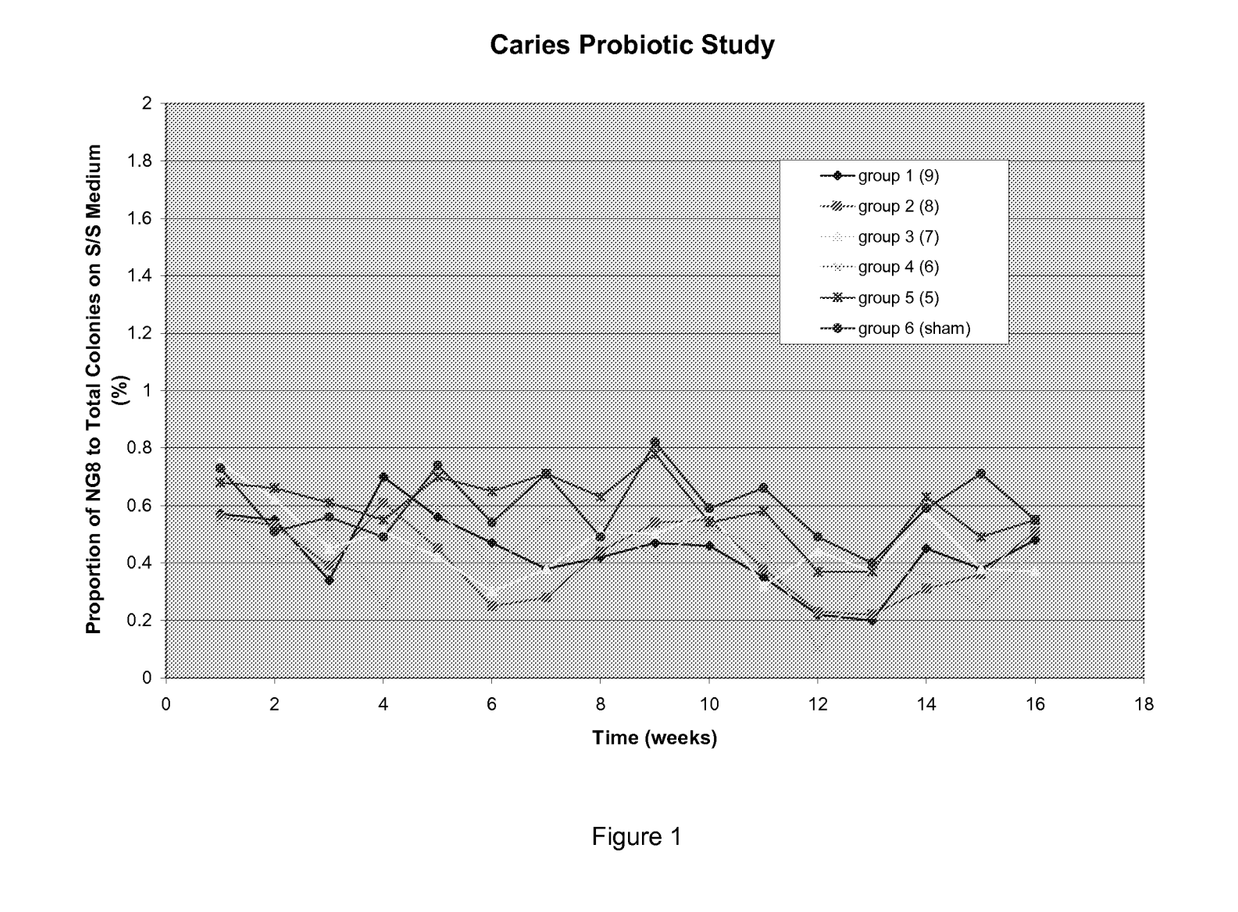
FIG. 1 shows the results of administration of daily treatment with JH145.

At weekly intervals, plaque and saliva were sampled using cotton tipped swabs, and samples plated on *S. mutans* screening/selection medium to selectively cultivate NG8 (white colonies) and JH145 (red colonies). Levels of NG8 were plotted as a function of time. See FIG. 1.

Using a Univariate Analysis of Variance (ANOVA) to examine differences among the six groups (i.e., 5 treatment and 1 control) during week 9, results indicated a significant group effect, $F(5, 63)=5.53$, $p<0.001$. The effect size (ES=0.31) and observed power (1=0.99) for this analysis indicated that there was a sufficient amount of power to detect this small effect between the groups. Follow up t tests with Bonferroni correction (p=0.01) were conducted using a priori planned comparisons, which tested each treatment group against the control. These analyses indicated that treatment groups 1-4 exhibited significantly less *S. mutans* NG8 expression relative to the control group, $t$'s $(1, 21) \geq 2.7$, $p \leq 0.01$.

Therefore, daily treatment of rats with $>10^6$ cells of JH145 results in decreased levels of indigenous *S. mutans*. A decreased risk of dental caries and improved dental health should follow. The effect of the treatment is likely to be significantly better in human subjects who would hold and swish the probiotic in their mouths for 30 to 60 seconds per treatment. Relative to the rat, which quickly swallows the probiotic preparation, the longer exposure of human teeth to JH145 should increase the opportunity for it to compete with indigenous *S. mutans*, resulting in improved effectiveness.

Human studies can be performed to verify that daily exposure with a suspension of *mutans* streptococci for example, *S. rattus* JH145 (ldh,str) results in decreased numbers of an indigenous *S. mutans* strain and cessation of the exposure results in eventual elimination of *S. rattus* JH145 and return of the indigenous *S. mutans* to original levels. Baseline levels of indigenous *S. mutans* can be determined. Daily doses of *S. rattus* JH145 can be administered to the oral cavity of the subjects. The oral flora of the subjects can be sampled weekly and wild-type *S. mutans* and *S. rattus* JH145 levels monitored until a decrease in wild-type *S. mutans* levels is observed. *S. rattus* JH145 doses are discontinued and oral flora is sampled weekly to follow decline in *S. rattus* JH145 levels and increase in wild-type *S. mutans* levels

*Streptococcus oralis* and *Streptococcus uberis* for Maintenance of Periodontal Health Human studies can be done to verify that daily exposure with a suspension of *S. oralis* (str) and/or *S. uberis* results in decreased numbers of indigenous periodontopathic species and cariogenic species and that cessation of the treatment results in eventual elimination of the *S. oralis* and/or *S. uberis* probiotic strain and return of the periodontopathic species and cariogenic species to original levels.

For example, baseline levels of 4 periodontopathic bacteria in saliva can be determined for human subjects. Daily doses of *S. oralis* and/or *S. uberis* can be administered to the oral cavity of human subjects. The oral flora of the human subjects can be sampled weekly to monitor pathogen and *S. oralis* and/or *S. uberis* levels until a decrease in levels of one or more pathogens is observed. The *S. oralis* and/or *S. uberis* doses are stopped and oral flora of the human subjects is sampled weekly to follow the decline in *S. oralis* and/or *S. uberis* levels and the corresponding increase in pathogen levels.

Finally, human studies and animal studies can be done to verify that daily exposure with a suspension of one or more isolated *S. oralis* (str) and/or *S. uberis* strains in combination with one or more isolated LDH-deficient *mutans streptococcus* strains results in decreased numbers of indigenous periodontopathic species and that cessation of the treatment results in eventual elimination of the probiotic strains and return of the periodontopathic species to original levels.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

What is claimed is:

1. A method of non-persistently colonizing an oral cavity of a subject, comprising:
   providing a probiotic formulation, comprising a bacterial formulation comprising an attenuated *Strep oralis* strain and a biologically pure *mutans streptococci* strain selected from the group consisting of *Streptococcus rattus, Streptococcus cricetus, Streptococcus mutans, Streptococcus sobrinus, Streptococcus downeii, Streptococcus macacae*, and *Streptococcus ferus*; wherein said *mutans streptococcus* strains are genetically modified strains that are lactate dehydrogenase-deficient; and
   applying the probiotic formulation to the oral cavity.

2. The method of claim 1, wherein the attenuated *Strep oralis* strain is streptomycin resistant.

3. The method of claim 1, wherein the probiotic formulation comprises a biologically pure *Streptococcus uberis* strain.

4. The method of claim 1, wherein the probiotic formulation is provided as a food formulation.

5. The method of claim 4, wherein the food formulation is provided in a form selected from the group consisting of a powdered food supplement, a paste, a gel, a solid food, a packaged food, a wafer, a lozenge, and a chewing gum.

6. The method of claim 4, wherein the food formulation comprises a nutritional component selected from the group consisting of a vitamin, a mineral, an amino acid, a carbohydrate, a lipid, and a dietary supplement.

7. The method of claim 4, wherein the food formulation comprises a flavoring.

8. The method of claim 4, wherein the food formulation comprises a food-quality coloring agent.

9. The method of claim 4, wherein the food formulation comprises a thickening agent.

10. The method of claim 7, wherein the food formulation comprises a thickening agent selected from the group consisting of corn starch, guar gum, carbopol, and xanthan gum.

11. A probiotic formulation for non-persistently colonizing an oral cavity of a subject, comprising:
   an attenuated *Strep oralis* strain; and
   a biologically pure *mutans streptococci* strain selected from the group consisting of *Streptococcus rattus, Streptococcus cricetus, Streptococcus mutans, Streptococcus sobrinus, Streptococcus downeii, Streptococcus macacae,* and *Streptococcus ferus*; wherein said *mutans streptococcus* strains are genetically modified strains that are lactate dehydrogenase-deficient,
   wherein the probiotic formulation comprises $10^3$ CFU to $10^{11}$ CFU of viable bacteria as a consumable portion.

12. The probiotic formulation of claim 11, wherein the attenuated *Strep oralis* strain is streptomycin resistant.

13. The probiotic formulation of claim 11, wherein the probiotic formulation comprises a biologically pure *Streptococcus uberis* strain.

14. The probiotic formulation of claim 11, wherein the probiotic formulation is provided as a food formulation.

15. The probiotic formulation of claim 14, wherein the food formulation is provided in a form selected from the group consisting of a powdered food supplement, a paste, a gel, a solid food, a packaged food, a wafer, a lozenge, and a chewing gum.

16. The probiotic formulation of claim 14, wherein the food formulation comprises a nutritional component selected from the group consisting of a vitamin, a mineral, an amino acid, a carbohydrate, a lipid, and a dietary supplement.

17. The probiotic formulation of claim 14, wherein the food formulation comprises a flavoring.

18. The probiotic formulation of claim 14, wherein the food formulation comprises a food-quality coloring agent.

19. The probiotic formulation of claim 14, wherein the food formulation comprises a thickening agent.

20. The probiotic formulation of claim 19, wherein the thickening agent is selected from the group consisting of corn starch, guar gum, carbopol, and xanthan gum.

* * * * *

SEQUENCE LISTING

```
<160> NUMBER OF SEQ ID NOS: 10

<210> SEQ ID NO 1
<211> LENGTH: 1283
<212> TYPE: DNA
<213> ORGANISM: Streptococcus mutans
```

<400> SEQUENCE: 1

```
tcacgaacat ctggcagggc acgagaaaca ataacactca tagcatagtc aataaaactc      60
gttttcattt cactcgttaa attaacatct actaaatttc tatcttgcat taaaaaatgc     120
tccatttcta gtctaaaact cctttatatt atatcacaaa aaatgctctt tttcagctat     180
tctactatag ttttccttta acagaggaaa atactagtga ctttttttaac aaaaagtgtt     240
agaataaatt cgtataaaat atacacttaa taaattataa ggagatgttt agaacatgac     300
tgcaactaaa caacataaaa aagtcatcct tgtcggtgat ggtgctgtag gatcatctta     360
cgccttcgcc cttgttaacc aaggaatcgc tcaagaactc ggaattattg aaattcctca     420
gctgtttgaa aaggctgttg gagacgctct tgaccttagc catgcacttg ccttcacttc     480
accaaagaaa atttacgctg ctaaatatga agactgtgcg gatgctgcct tgttgtcatt     540
actgcaggtg cacctcaaaa accaggtgaa actcgtcttg accttgtcgg taaaaacctt     600
gcaatcaaca aatctatcgt tacacaagtg gttgaatcag gctttaaggg aatcttcttg     660
gttgctgcca acccagttga catcttgact tattcaacat ggaaattctc aggtttccct     720
aaagaacgcg tcattggttc tggtacatct cttgatactg ctcgtttccg tcaagctctt     780
gctgaaaaaa tcggggttga tgctcggtca gtccacgcct atatcatggg tgaacacggt     840
gattcagaat tgccgtttg gtctcatgcc aatgtagctg gtgttaaatt agaacaatgg     900
ctgcaagaca accgtgatgt tgatgctgaa ggtctcgtaa aactgtttgt atctgttcgt     960
gatgctgctt attcaatcat caacaaaaaa ggtgctactt tctatggtat cgctgtcgcc    1020
cttgcccgta tcactaaagc aatcttggat gacgaaaacg ccgttcttcc gctttcagtt    1080
ttccaatcag gccaatacga aggtgttgaa gatgtcttca tcggacagcc ggccatcgtt    1140
ggtgcacacg gtatcgttcg tccagtaaat attccgttaa atgatgctga actgcaaaaa    1200
atgcaggctt ctgctaaaca gctgaaagca atcattgacg aagctttctc aaatgaagaa    1260
tttgctgctg ctgcagctcg taa                                            1283
```

<210> SEQ ID NO 2
<211> LENGTH: 130
<212> TYPE: PRT
<213> ORGANISM: Streptococcus mutans

<400> SEQUENCE: 2

```
Met Thr Ala Thr Lys Gln His Lys Lys Val Ile Leu Val Gly Asp Gly
1               5                   10                  15

Ala Val Gly Ser Ser Tyr Ala Phe Ala Leu Val Asn Gln Gly Ile Ala
            20                  25                  30

Gln Glu Leu Gly Ile Ile Glu Ile Pro Gln Leu Phe Glu Lys Ala Val
        35                  40                  45

Gly Asp Ala Leu Asp Leu Ser His Ala Leu Ala Phe Thr Ser Pro Lys
    50                  55                  60

Lys Ile Tyr Ala Ala Lys Tyr Glu Asp Cys Ala Asp Ala Ala Leu Leu
65                  70                  75                  80

Ser Leu Leu Gln Val His Leu Lys Asn Gln Val Lys Leu Val Leu Thr
                85                  90                  95

Leu Ser Val Lys Thr Leu Gln Ser Thr Asn Leu Ser Leu His Lys Trp
            100                 105                 110

Leu Asn Gln Ala Leu Arg Glu Ser Ser Trp Leu Leu Pro Thr Gln Leu
        115                 120                 125

Thr Ser
```

-continued

130

<210> SEQ ID NO 3
<211> LENGTH: 62
<212> TYPE: PRT
<213> ORGANISM: Streptococcus mutans

<400> SEQUENCE: 3

Leu Ile Gln His Gly Asn Ser Gln Val Ser Leu Lys Asn Ala Ser Leu
1               5                   10                  15

Val Leu Val His Leu Leu Ile Leu Val Ser Val Lys Leu Leu
            20                  25                  30

Lys Lys Ser Gly Leu Met Leu Gly Gln Ser Thr Pro Ile Ser Trp Val
            35                  40                  45

Asn Thr Val Ile Gln Asn Leu Pro Phe Gly Leu Met Pro Met
    50                  55                  60

<210> SEQ ID NO 4
<211> LENGTH: 4
<212> TYPE: PRT
<213> ORGANISM: Streptococcus mutans

<400> SEQUENCE: 4

Leu Val Leu Asn
1

<210> SEQ ID NO 5
<211> LENGTH: 15
<212> TYPE: PRT
<213> ORGANISM: Streptococcus mutans

<400> SEQUENCE: 5

Asn Asn Gly Cys Lys Thr Thr Val Met Leu Met Leu Lys Val Ser
1               5                   10                  15

<210> SEQ ID NO 6
<211> LENGTH: 75
<212> TYPE: PRT
<213> ORGANISM: Streptococcus mutans

<400> SEQUENCE: 6

Asn Cys Leu Tyr Leu Phe Val Met Leu Leu Ile Gln Ser Ser Thr Lys
1               5                   10                  15

Lys Val Leu Leu Ser Met Val Ser Leu Ser Pro Leu Pro Val Ser Leu
            20                  25                  30

Lys Gln Ser Trp Met Thr Lys Thr Pro Phe Phe Arg Phe Gln Phe Ser
            35                  40                  45

Asn Gln Ala Asn Thr Lys Val Leu Lys Met Ser Ser Ser Asp Ser Arg
    50                  55                  60

Pro Ser Leu Val His Thr Val Ser Phe Val Gln
65                  70                  75

<210> SEQ ID NO 7
<211> LENGTH: 14
<212> TYPE: PRT
<213> ORGANISM: Streptococcus mutans

<400> SEQUENCE: 7

Met Met Leu Asn Cys Lys Lys Cys Arg Leu Leu Leu Asn Ser
1               5                   10

```
<210> SEQ ID NO 8
<211> LENGTH: 19
<212> TYPE: PRT
<213> ORGANISM: Streptococcus mutans

<400> SEQUENCE: 8
```

Lys Gln Ser Leu Thr Lys Leu Ser Gln Met Lys Asn Leu Leu Leu
1               5                   10                  15

Gln Leu Val

```
<210> SEQ ID NO 9
<211> LENGTH: 1283
<212> TYPE: DNA
<213> ORGANISM: Streptococcus mutans

<400> SEQUENCE: 9
```

| | | | | | |
|---|---|---|---|---|---|
| tcacgaacat | ctggcagggc | acgagaaaca | ataacactca | tagcatagtc | aataaaactc | 60 |
| gttttcattt | cactcgttaa | ataacatcta | ctaaatttct | atcttgcatt | aaaaaatgct | 120 |
| ccatttctag | tctaaaactc | ctttatatta | tatcacaaaa | aatgctcttt | ttcagctatt | 180 |
| ctactatagt | tttcctttaa | cagaggaaaa | tactagtgac | ttttttaaca | aaaagtgtta | 240 |
| gaataaattc | gtataaaata | tacacttaat | aaattataag | gagatgttta | gaacatgact | 300 |
| gcaactaaac | aacataaaaa | agtcatcctt | gtcggtgatg | gtgctgtagg | atcatcttac | 360 |
| gccttcgccc | ttgttaacca | aggaatcgct | caagaactcg | gaattattga | aattcctcag | 420 |
| ctgtttgaaa | aggctgttgg | agacgctctt | gaccttagcc | atgcacttgc | cttcacttca | 480 |
| ccaaagaaaa | tttacgctgc | taaatatgaa | gactgtgcgg | atgctgacct | tgttgtcatt | 540 |
| actgcaggtg | cacctcaaaa | accaggtgaa | actcgtcttg | accttgtcgg | taaaaacctt | 600 |
| gcaatcaaca | aatctatcgt | tacacaagtg | gttgaatcag | gctttaaggg | aatcttcttg | 660 |
| gttgctgcca | acccagttga | catcttgact | tattcaacat | ggaaattctc | aggtttccct | 720 |
| aaagaacgcg | tcattggttc | tggtacatct | cttgatactg | ctcgtttccg | tcaagctctt | 780 |
| gctgaaaaaa | tcggggttga | tgctcggtca | gtccacgcct | atatcatggg | tgaacacggt | 840 |
| gattcagaat | tgccgttttg | gtctcatgcc | aatgtagctg | tgttaaatt | agaacaatgg | 900 |
| ctgcaagaca | accgtgatgt | tgatgctgaa | ggtctcgtaa | aactgtttgt | atctgttcgt | 960 |
| gatgctgctt | attcaatcat | caacaaaaaa | ggtgctactt | tctatggtat | cgctgtcgcc | 1020 |
| cttgcccgta | tcactaaagc | aatcttggat | gacgaaaacg | ccgttcttcc | gctttcagtt | 1080 |
| ttccaatcag | gccaatacga | aggtgttgaa | gatgtcttca | tcggacagcc | ggccatcgtt | 1140 |
| ggtgcacacg | gtatcgttcg | tccagtaaat | attccgttaa | atgatgctga | actgcaaaaa | 1200 |
| atgcaggctt | ctgctaaaca | gctgaaagca | atcattgacg | aagctttctc | aaatgaagaa | 1260 |
| tttgctgctg | ctgcagctcg | taa | | | | 1283 |

```
<210> SEQ ID NO 10
<211> LENGTH: 329
<212> TYPE: PRT
<213> ORGANISM: Streptococcus mutans

<400> SEQUENCE: 10
```

Met Thr Ala Thr Lys Gln His Lys Lys Val Ile Leu Val Gly Asp Gly
1               5                   10                  15

Ala Val Gly Ser Ser Tyr Ala Phe Ala Leu Val Asn Gln Gly Ile Ala
                20                  25                  30

Gln Glu Leu Gly Ile Ile Glu Ile Pro Gln Leu Phe Glu Lys Ala Val

-continued

```
              35                  40                  45
Gly Asp Ala Leu Asp Leu Ser His Ala Leu Ala Phe Thr Ser Pro Lys
     50                  55                  60

Lys Ile Tyr Ala Ala Lys Tyr Glu Asp Cys Ala Asp Ala Asp Leu Val
65                   70                  75                  80

Val Ile Thr Ala Gly Ala Pro Gln Lys Pro Gly Glu Thr Arg Leu Asp
                 85                  90                  95

Leu Val Gly Lys Asn Leu Ala Ile Asn Lys Ser Ile Val Thr Gln Val
            100                 105                 110

Val Glu Ser Gly Phe Lys Gly Ile Phe Leu Val Ala Ala Asn Pro Val
        115                 120                 125

Asp Ile Leu Thr Tyr Ser Thr Trp Lys Phe Ser Gly Phe Pro Lys Glu
    130                 135                 140

Arg Val Ile Gly Ser Gly Thr Ser Leu Asp Thr Ala Arg Phe Arg Gln
145                 150                 155                 160

Ala Leu Ala Glu Lys Ile Gly Val Asp Ala Arg Ser Val His Ala Tyr
                165                 170                 175

Ile Met Gly Glu His Gly Asp Ser Glu Phe Ala Val Trp Ser His Ala
            180                 185                 190

Asn Val Ala Gly Val Lys Leu Glu Gln Trp Leu Gln Asp Asn Arg Asp
        195                 200                 205

Val Asp Ala Glu Gly Leu Val Lys Leu Phe Val Ser Val Arg Asp Ala
    210                 215                 220

Ala Tyr Ser Ile Ile Asn Lys Lys Gly Ala Thr Phe Tyr Gly Ile Ala
225                 230                 235                 240

Val Ala Leu Ala Arg Ile Thr Lys Ala Ile Leu Asp Asp Glu Asn Ala
                245                 250                 255

Val Leu Pro Leu Ser Val Phe Gln Ser Gly Gln Tyr Glu Gly Val Glu
            260                 265                 270

Asp Val Phe Ile Gly Gln Pro Ala Ile Val Gly Ala His Gly Ile Val
        275                 280                 285

Arg Pro Val Asn Ile Pro Leu Asn Asp Ala Glu Leu Gln Lys Met Gln
    290                 295                 300

Ala Ser Ala Lys Gln Leu Lys Ala Ile Ile Asp Glu Ala Phe Ser Asn
305                 310                 315                 320

Glu Glu Phe Ala Ala Ala Ala Arg
                325
```